United States Patent [19]
Lafontaine et al.

[11] Patent Number: 5,695,468
[45] Date of Patent: Dec. 9, 1997

[54] BALLOON CATHETER WITH IMPROVED PRESSURE SOURCE

[75] Inventors: Daniel M. Lafontaine, Plymouth; Chad J. Kugler, Spring Lake Park; Matthew M. Burns, Orono, all of Minn.

[73] Assignee: SCIMED Life Systems, Inc., Maple Grove, Minn.

[21] Appl. No.: 586,514

[22] Filed: Jan. 16, 1996

Related U.S. Application Data

[63] Continuation-in-part of Ser. No. 308,025, Sep. 16, 1994, Pat. No. 5,545,133.
[51] Int. Cl.$^6$ .................................................. A61M 29/00
[52] U.S. Cl. ..................... 604/96; 604/99; 606/192
[58] Field of Search .................... 604/96, 97, 99, 604/100, 186, 101; 606/192–195

[56] References Cited

U.S. PATENT DOCUMENTS

| | | |
|---|---|---|
| 3,190,291 | 6/1965 | Foley . |
| 3,378,011 | 4/1968 | Vitello . |
| 3,379,197 | 4/1968 | Hayes . |
| 3,602,226 | 8/1971 | Ericson . |
| 3,675,658 | 7/1972 | Taylor . |
| 3,726,283 | 4/1973 | Dye et al. . |
| 3,818,903 | 6/1974 | Bleecker . |
| 4,227,534 | 10/1980 | La Rosa . |
| 4,244,366 | 1/1981 | Raines . |
| 4,446,867 | 5/1984 | Leveen et al. . |
| 4,476,866 | 10/1984 | Chin . |
| 4,479,497 | 10/1984 | Fogarty et al. . |
| 4,535,757 | 8/1985 | Webster, Jr. . |
| 4,564,014 | 1/1986 | Fogarty et al. . |
| 4,592,364 | 6/1986 | Pinto . |
| 4,593,690 | 6/1986 | Sheridan et al. . |

(List continued on next page.)

FOREIGN PATENT DOCUMENTS

| | | |
|---|---|---|
| 2 209 121 | 5/1989 | United Kingdom . |
| WO 92/03095 | 3/1992 | WIPO . |
| WO 93/17750 | 9/1993 | WIPO . |

OTHER PUBLICATIONS

*Therapy and Prevention Congenital Heart Disease*, AHA Circulatin brochure, "Angioplasty for coarctation of the aorta: long–term results", R. Cooper et al.; vol. 75, No. 3, pp. 600–604, Mar. 1987.

*European Heart Journal*, "Anterograde percutaneous transseptal valvuloplasty in a case of severe calcific aortic stenosis", vol. 8, pp. 190–192, Feb. 1987.

*Clinical Cardiology*, "Balloon Aortic Valvuloplasty in Children", vol. 13, pp. 458–466, Jul. 1990.

"Balloon Catheters and Transluminal Dilatation: Technical Considerations," John Abele, *American Journal of Roentgenology*, vol. 135, pp. 901–906, Nov. 1980.

(List continued on next page.)

Primary Examiner—John D. Yasko
Attorney, Agent, or Firm—Robert E. Atkinson

[57] ABSTRACT

A balloon catheter is disclosed which includes a fluid displacement rod at least partially and slidably disposed in an elongate tubular member with a balloon connected to the distal end of the tubular member. A seal connected to the proximal end of the tubular member creates a liquid tight seal between the inside of the tubular member and the displacement rod. Accordingly, longitudinal actuation of the displacement rod causes the balloon to expand and/or contract. The balloon catheter may be a fixed wire, an over-the-wire or a single-operator exchange type balloon catheter. In addition, a pressure gauge may be connected to the proximal end of the tubular member. A one-way valve is also disclosed which allows the balloon catheter to be prepped via the guide wire lumen. Accordingly, the present invention negates the need for both an inflation device and an inflation lumen which results in a significant improvement in catheter performance and cost savings.

29 Claims, 11 Drawing Sheets

U.S. PATENT DOCUMENTS

| | | |
|---|---|---|
| 4,651,738 | 3/1987 | Demer et al. . |
| 4,652,259 | 3/1987 | O'Neil . |
| 4,655,749 | 4/1987 | Fischione . |
| 4,740,203 | 4/1988 | Hoskins et al. . |
| 4,758,223 | 7/1988 | Rydell . |
| 4,762,130 | 8/1988 | Fogarty et al. . |
| 4,781,192 | 11/1988 | Demer . |
| 4,838,864 | 6/1989 | Peterson . |
| 4,878,903 | 11/1989 | Mueller . |
| 4,929,238 | 5/1990 | Baum . |
| 4,930,341 | 6/1990 | Euteneuer . |
| 4,944,726 | 7/1990 | Hilal et al. . |
| 4,954,239 | 9/1990 | Mueller . |
| 5,004,472 | 4/1991 | Wallace . |
| 5,009,662 | 4/1991 | Wallace et al. . |
| 5,019,041 | 5/1991 | Robinson et al. . |
| 5,021,046 | 6/1991 | Wallace . |
| 5,035,705 | 7/1991 | Burns . |
| 5,049,130 | 9/1991 | Powell . |
| 5,100,385 | 3/1992 | Bromander . |
| 5,113,868 | 5/1992 | Wise et al. . |
| 5,152,277 | 10/1992 | Honda et al. . |
| 5,152,776 | 10/1992 | Pinchuk . |
| 5,156,598 | 10/1992 | Skakoon et al. . |
| 5,171,299 | 12/1992 | Heitzmann et al. . |
| 5,180,364 | 1/1993 | Ginsburg . |
| 5,180,367 | 1/1993 | Kontos et al. . |
| 5,196,017 | 3/1993 | Silva et al. . |
| 5,209,728 | 5/1993 | Kraus et al. . |
| 5,215,523 | 6/1993 | Williams et al. . |
| 5,217,434 | 6/1993 | Arney . |
| 5,242,398 | 9/1993 | Knoll . |
| 5,246,420 | 9/1993 | Kraus et al. . |
| 5,265,593 | 11/1993 | Odland . |
| 5,273,529 | 12/1993 | Idowu . |
| 5,273,537 | 12/1993 | Haskvitz et al. . |
| 5,275,169 | 1/1994 | Afromowitz et al. . |
| 5,284,480 | 2/1994 | Porter et al. . |
| 5,306,261 | 4/1994 | Alliger et al. . |
| 5,318,533 | 6/1994 | Adams et al. . |
| 5,334,153 | 8/1994 | McIntyre et al. . |
| 5,338,301 | 8/1994 | Diaz . |
| 5,378,238 | 1/1995 | Peters et al. . |

OTHER PUBLICATIONS

"Angiographic Patterns of Balloon Inflation During Percutaneous Transluminal Coronary Angioplasty: Role of Pressure–Diameter Curves in Studying Distensibility and Elasticity of the Stenotic Lesion and the Mechanism of Dilation," Hjemdahl–Monsen et al., *Journal of the American College of Cardiology*, vol. 16, No. 3, pp. 569–575, Sep. 1990.

"High Intensity Ultrasound Increases Distensibility of Calcific Atherosclerotic Arteries," Demer et al., *Journal of the American College of Cardiology*, vol. 18, No. 5, pp. 1259–1262, Nov. 1991.

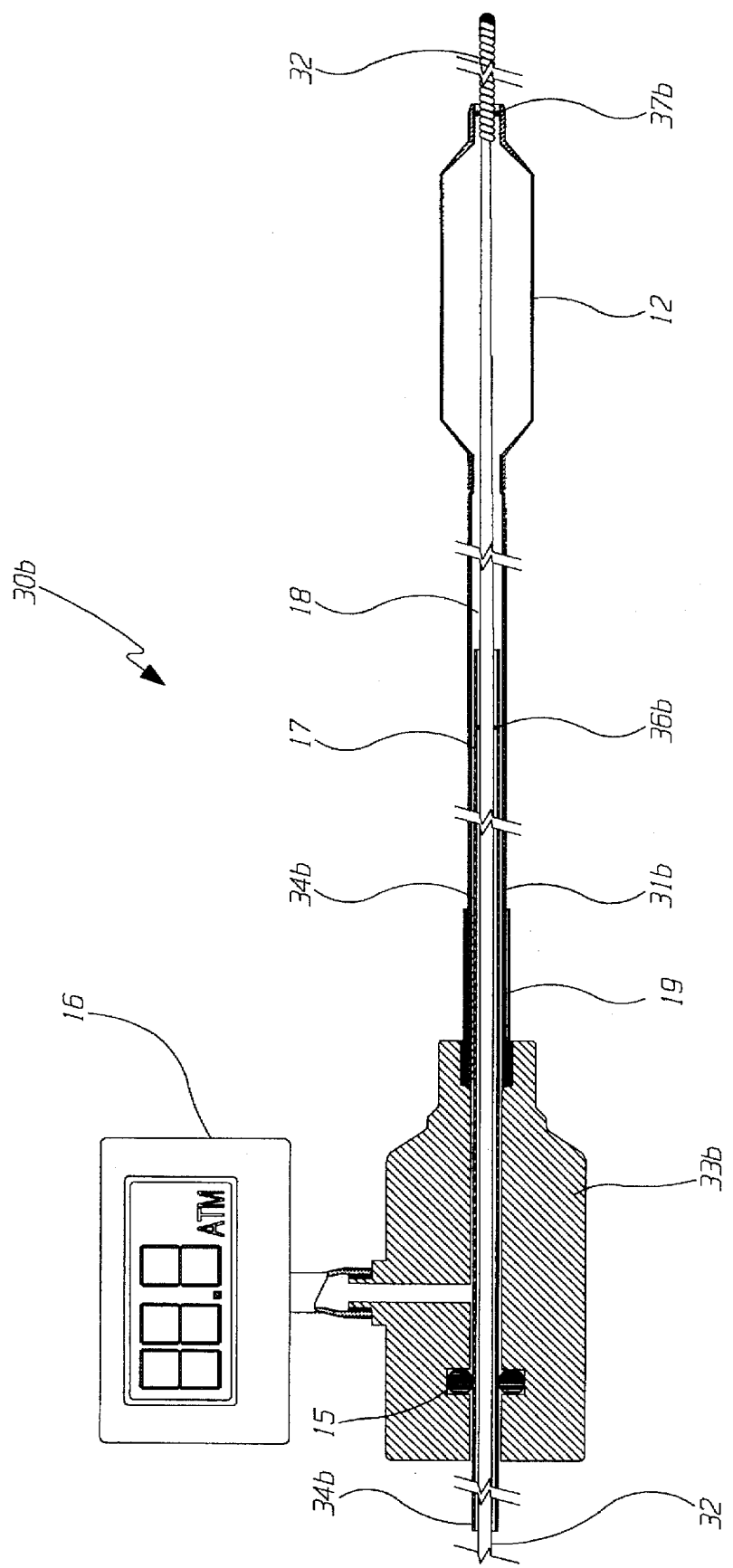

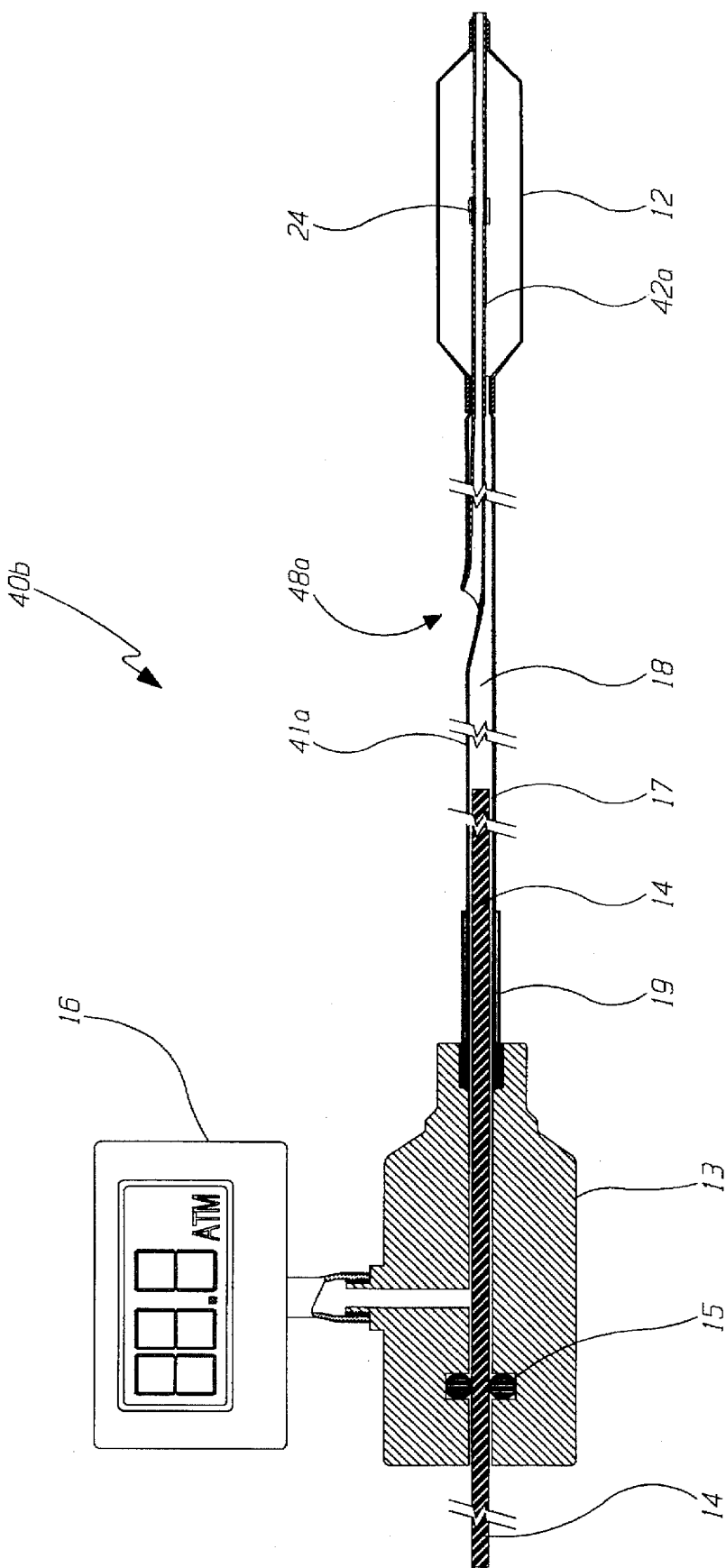

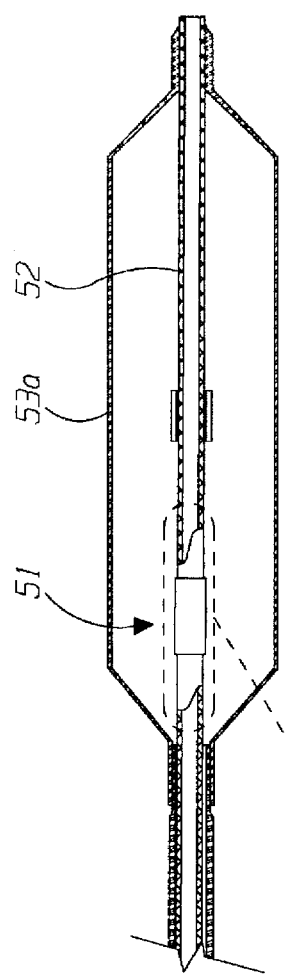
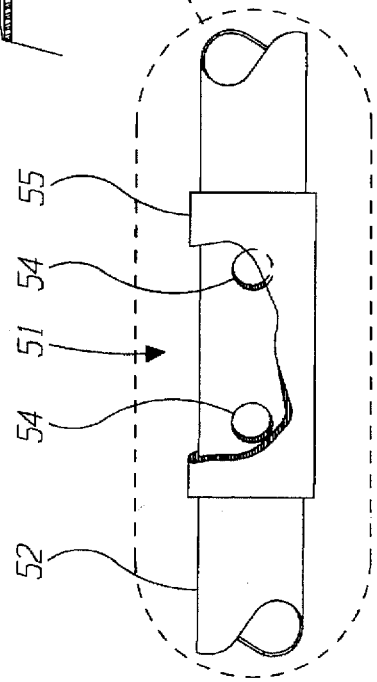
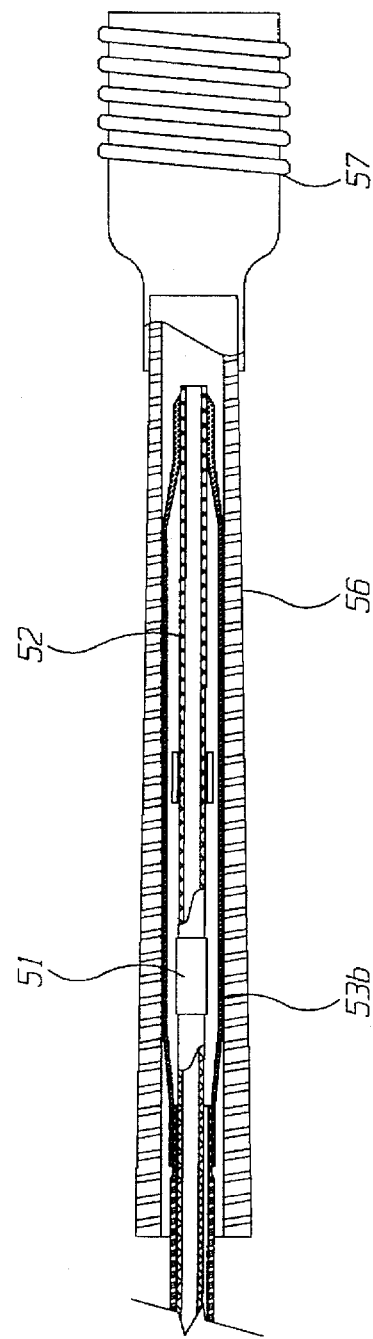
FIGURE 5a
FIGURE 5b
FIGURE 5c

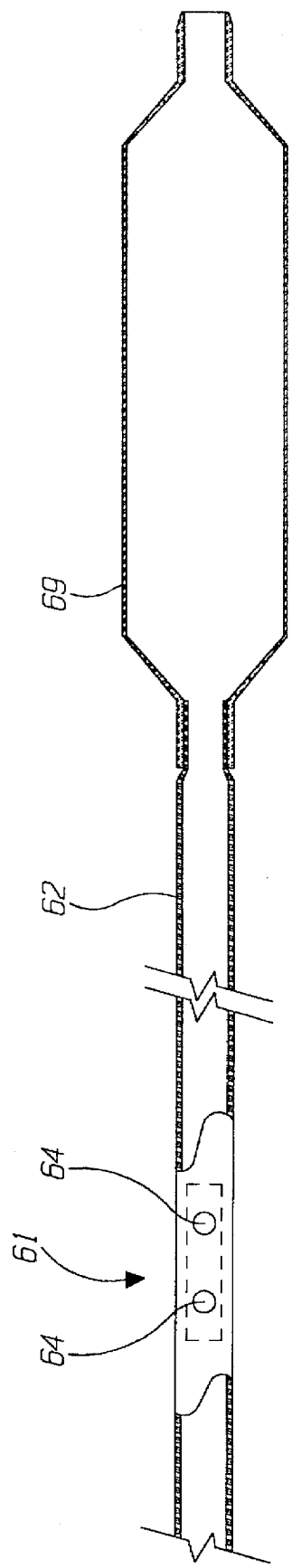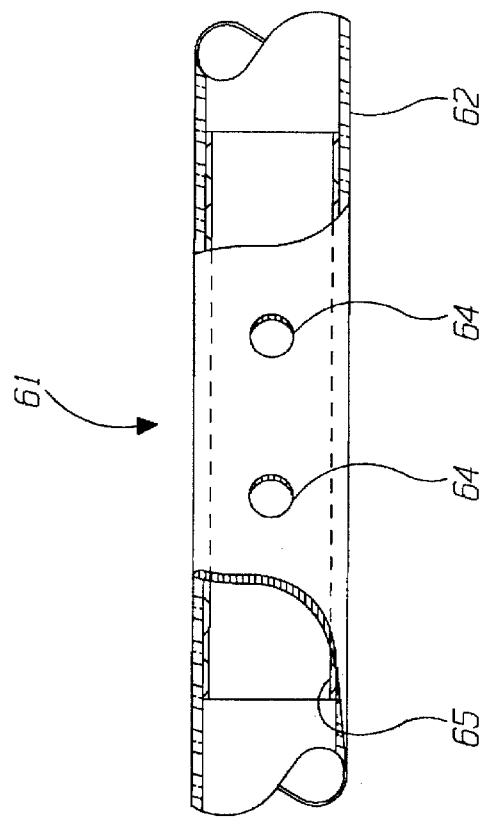
FIGURE 6a
FIGURE 6b

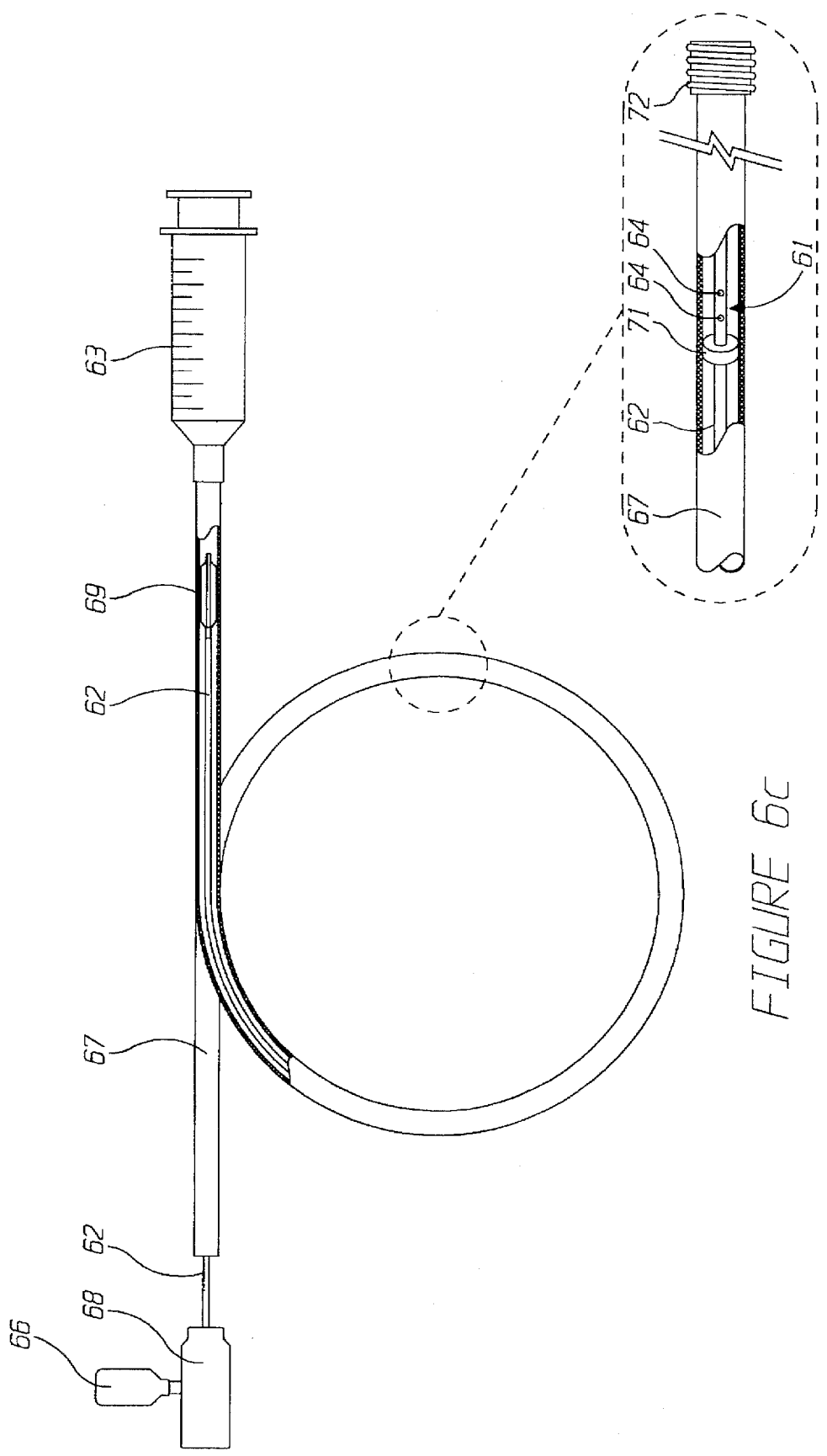

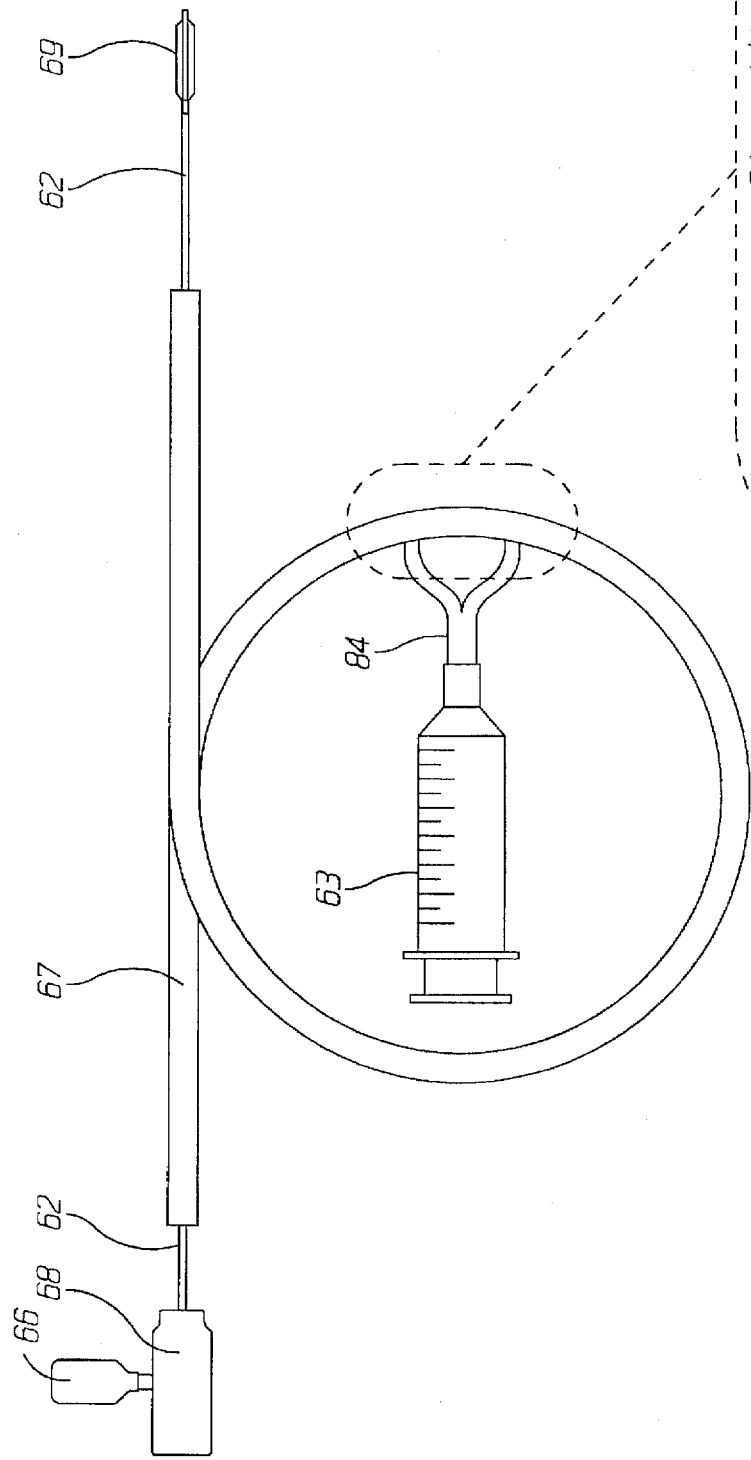
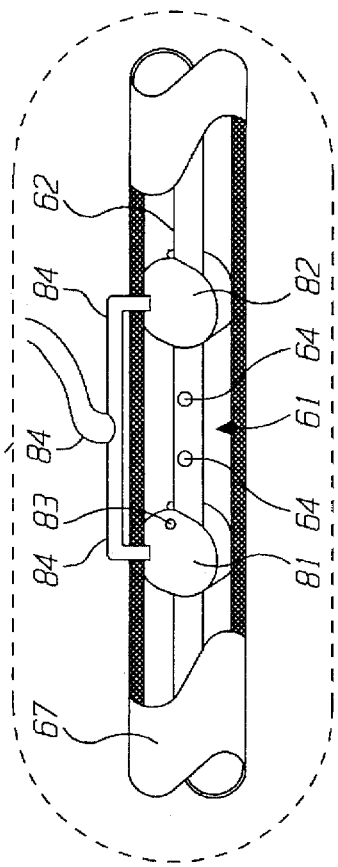
FIGURE 6e
FIGURE 6f

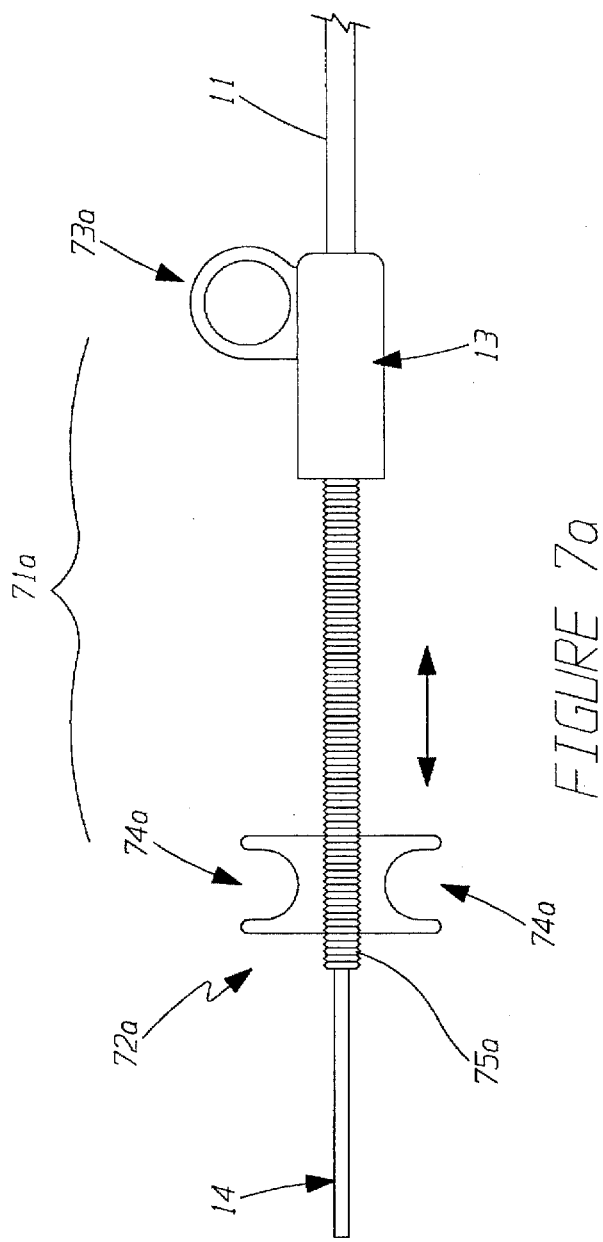
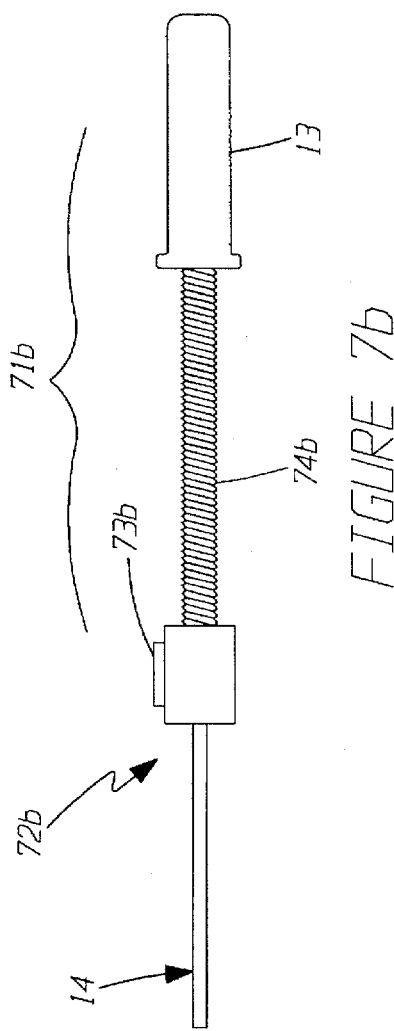

BALLOON CATHETER WITH IMPROVED PRESSURE SOURCE

CROSS-REFERENCE TO RELATED APPLICATIONS

This application is a continuation-in-part of patent application Ser. No. 08/308,025 filed on Sep. 16, 1994, now U.S. Pat. No. 5,545,133 entitled BALLOON CATHETER WITH IMPROVED PRESSURE SOURCE, the entire disclosure of which is hereby incorporated by reference.

FIELD OF THE INVENTION

The present invention generally relates to balloon catheters. More specifically, the present invention relates to balloon dilation catheters used for the treatment of vascular disease. Those skilled in the art will recognize the benefits of applying the present invention to similar fields not discussed herein.

BACKGROUND OF THE INVENTION

A wide variety of therapeutic techniques have been developed to correct or inhibit vascular diseases. Coronary artery disease (CAD), for example, is an adverse condition of the heart in which the blood flow to the heart muscle is partially or totally restricted by occlusive material in the coronary arteries which narrows the blood flow lumen. The occlusive materials deprive portions of the heart muscle of essential oxygenated blood.

CAD may be treated by a surgical technique referred to as coronary artery bypass graft (CABG) surgery. This surgical procedure involves supplementing blood flow to the heart muscle by grafting a non-native conduit such as a saphenous vein graft (SVG) to the heart. A first end of the SVG is connected to the ascending aorta (proximal to the occlusive material) and the other end is connected to the artery distal of the occlusive material. Although this technique has been useful for treating CAD in native coronary arteries, it is not uncommon for occlusive material to form over time in the SVG thereby necessitating additional therapy.

Percutaneous translumenal coronary angioplasty (PTCA) has gained wide acceptance as an effective and less invasive alternative to CABG surgery in certain patient groups. The PTCA procedure involves the use of an angioplasty balloon catheter, several types of which are well known in the art. The balloon catheter is inserted into the body via the femoral artery and navigated to the coronary arteries assisted by a guide catheter and (usually) a guide wire. The balloon is positioned across the restriction in the artery and subsequently inflated. The inflated balloon widens the restriction and restores blood flow to portions of the heart muscle previously deprived of oxygenated blood.

A PTCA balloon catheter is typically about 135 to 150 cm long and has a manifold at its proximal end and a balloon at its distal end. The manifold facilitates connection to an inflation device which is used to inflate and deflate the balloon. A conventional PTCA balloon catheter also includes an inflation lumen extending through its entire length to facilitate the delivery of inflation fluid to and from the balloon. Depending on the type of catheter used, an inflation lumen may be circular in cross section or it may be annular in cross section. Some catheters have an inflation lumen which is circular at the proximal end of the shaft and annular at the distal end of the shaft. Since PTCA catheters are relatively small in profile in order to facilitate navigation through the vascular system, the inflation lumen extending through the shaft is proportionately small. The long length of a typical inflation lumen in combination with its relatively small size create a significant resistance to the flow of inflation fluid. Consequently, the time required to inflate and deflate the balloon is also long. Because flow rates are proportional to pressure, the drag on the inflation fluid is particularly noticeable during balloon deflation when the maximum possible pressure gradient is 14.7 psi. The deflation time is clinically significant because an excessively long deflation time will compromise the treating physician's ability to relieve aschemia and/or reestablish blood flow across the occlusion being dilated. Furthermore, the compliance of the inflation fluid, the inflation device and the entire structure defining the fluid path add to the delay in balloon deflation and inflation. The compliance of the fluid system reduces the immediate responsiveness of the balloon to actuation of the inflation device.

An inflation device is typically capable of inflating to pressures of about 300 psi, and is capable of drawing a near perfect vacuum (perfect vacuum=—14.7 psi). An inflation device is usually in the form of a modified 20 cc syringe and typically includes a threaded plunger with a handle and lock mechanism, and a pressure gauge. Due to its size and weight, a typical inflation device is extremely bulky as compared to a PTCA catheter.

Prior art balloon dilation catheters and inflation devices have certain disadvantages which are desirable to overcome. For example, it is desirable to reduce the inflation/deflation time of a balloon catheter and increase the immediate responsiveness of the balloon. This would allow for a more rapid balloon deflation and thus relieve aschemia and other adverse reactions to prolonged balloon inflation. Reducing inflation/deflation time would also allow for more effective use of the pulsating balloon technique. Eliminating a significant amount of the fluid system compliance would allow the treating physician to better "feel" the response of the vascular restriction to the inflation of the balloon. These desirable aspects would improve the treating physician's capabilities to treat CAD.

It is also desirable to eliminate the need to use a bulky inflation device. Eliminating the need for an inflation device would, for example, reduce the number accessory devices needed in a procedure, reduce the number prepping procedures required, reduce the necessary storage space, and reduce the amount of medical waste generated in a procedure. All of these benefits would ultimately save a significant amount of time and expense on behalf of the treating physician, the medical support staff, the hospital and the patient.

SUMMARY OF THE INVENTION

The present invention overcomes the disadvantages of the prior art and provides the desirable features outlined above by eliminating the need for an inflation device and an inflation lumen. In particular, the present invention, inter alia, reduces the drag on inflation fluid and reduces the compliance of the inflation system. The reduction in drag and compliance correlates to an increase in balloon responsiveness which may be clinically significant for the reasons discussed previously. Eliminating the need for an inflation device and an inflation lumen also correlates to savings of time and money.

Broadly stated, the present invention may be described as a balloon catheter which includes a sealed chamber in fluid communication with a distally mounted balloon and a fluid displacement member disposed at least partially within the sealed chamber to displace fluid into or out of the balloon.

Specifically, one embodiment of the present invention is a balloon catheter which includes a long tubular member having a balloon connected to it's distal end. A fluid displacement rod is at least partially and slidably disposed in the tubular member such that the balloon may be expanded when the rod is slid into the tubular member. A seal is connected to the proximal end of the tubular member and disposed about the displacement rod to create a liquid seal between the inside of the tubular member and the displacement rod. The seal may, for example, be an o-ring type seal or a gap tolerance type seal. A pressure gauge may be connected to the proximal end of the elongate tubular member to measure pressure inside the balloon. The balloon catheter may be a fixed wire, an over-the-wire or a single-operator-exchange type balloon catheter.

If the balloon catheter is an over-the-wire or a single-operator-exchange type balloon catheter, a one-way-valve may be connected to the distal end of the tubular member to permit fluid to flow from the guide wire lumen to the interior of the balloon and to prevent fluid from flowing from the interior of the balloon to the guide wire lumen. The valve may be connected to a portion of the tubular member traversing the interior of the balloon and the valve may include an elastomer tube disposed about a hole in the tubular member under the balloon.

The one-way-valve provides a means to prep the catheter (i.e., replace all the air in the catheter with liquid) prior to use in-vivo. One end of the guide wire lumen (e.g., the proximal end) may be plugged and the other end of the guide wire lumen (e.g., the distal end) may be connected to a pressurized liquid source such as a liquid filled syringe to facilitate the prepping process. The pressurized liquid source may be connected to the distal end of the guide wire lumen with a tubular member disposed about the balloon and the tubular member may retain the balloon in a contracted state (sometimes referred to as a balloon protector).

The present invention may also be described as a method of using a balloon catheter including the following steps: (1) providing a balloon catheter (wherein the balloon catheter includes a long tubular member having a balloon connected to it's distal end, a fluid displacement rod at least partially and slidably disposed in the tubular member, and a seal connected to the proximal end of the tubular member and disposed about the displacement rod); (2) inserting the balloon catheter into a vascular system of a patient; (3) positioning the balloon catheter adjacent a treatment site in the vascular system; (4) displacing the rod to at least partially expand the balloon; (5) displacing the rod to at least partially contract the balloon; and (6) withdrawing the balloon catheter from the vascular system.

Another embodiment of the present invention is a balloon catheter which includes a long shaft having a lumen disposed therein which extends from a point distal of the proximal end of the shaft to the distal end of the shaft. A balloon is connected to the distal end of the shaft and a one-way-valve is also connected to the distal end of the shaft. The one-way-valve provides a means to prep the catheter (i.e., replace all the air in the catheter with liquid) prior to use in-vivo. In particular, the one-way-valve permits fluid to flow from the lumen to the interior of the balloon while preventing fluid to flow from the interior of the balloon to the lumen. The valve may be connected to a portion of the tubular member traversing the interior of the balloon and the valve may include an elastomer tube disposed about a hole in the tubular member under the balloon. One end of the lumen (e.g., the proximal end) may be plugged and the other end of the lumen (e.g., the distal end) may be connected to a pressurized liquid source such as a liquid filled syringe to facilitate the prepping process. The pressurized liquid source may be connected to the distal end of the lumen with a tubular member disposed about the balloon and the tubular member may retain the balloon in a contracted state.

The present invention may also be described as a method of prepping a balloon catheter including the following steps: (1) providing a balloon catheter (where the balloon catheter includes a long shaft with a lumen disposed therein, a balloon connected to the distal end of the shaft and a one-way-valve also connected to the distal end of the shaft); (2) providing a pressurized fluid source containing fluid therein (such as a fluid filled syringe); (3) connecting the pressurized fluid source to the distal end of the balloon catheter; (4) plugging the proximal end of the balloon catheter; and (5) forcing fluid from the pressurized fluid source into the catheter such that the fluid passes into the tubular member, through the one-way-valve and into the interior of the balloon.

Other aspects and advantages of the present invention can be fully appreciated with a thorough review of the entire specification and drawings. Those skilled in the art will appreciate other advantages not fully described herein. Furthermore, while the disclosure focuses on balloon catheters, those skilled in the art will recognize that the invention may be incorporated into other devices and methods of use without departing from the spirit of the invention.

BRIEF DESCRIPTION OF THE DRAWINGS

FIGS. 2, 3a, 3b, 4a and 4b show specific examples of catheter embodiments utilizing some of the generic features shown in FIG. 1. In particular, FIG. 2 shows a partially-sectioned side view of a fixed wire catheter embodiment. FIGS. 3a and 3b show, respectively, partially-sectioned side views of a side-by-side lumen over-the-wire catheter embodiment and a coaxial over-the-wire catheter embodiment. FIGS. 4a and 4b show partially-sectioned side views of two single-operator-exchange catheter embodiments.

FIG. 5a shows a partially-sectioned side view of a one-way valve incorporated into the distal section of either an over-the-wire or a single-operator-exchange catheter. FIG. 5b shows a detailed view of the one-way valve and FIG. 5c shows a tubular fitting over the distal end of the balloon catheter to facilitate prepping the balloon catheter via the one-way valve.

FIG. 6a shows a partially-sectioned side view of the distal section of a generic catheter incorporating a one-way valve proximal of the balloon. FIG. 6b shows a detailed view of the one-way valve. FIG. 6c shows a first embodiment of a system facilitating prepping a balloon catheter, utilizing a one-way valve as shown in FIGS. 6a and 6b. FIG. 6d shows a detailed view of the passive seal utilized in the prepping system shown in FIG. 6c. FIG. 6e shows a second embodiment of a system facilitating prepping a balloon catheter utilizing a one-way valve as shown in FIGS. 6a and 6b. FIG. 6f shows a detailed view of the active seals used in the prepping system shown in FIG. 6e.

FIGS. 7a and 7b show plan views of two mechanisms which facilitate manipulation of the fluid displacement rod.

DETAILED DESCRIPTION OF THE INVENTION

The following detailed description should be read with reference to the drawings in which similar parts in different drawings are numbered the same. The drawings, which are not necessarily to scale, depict exemplary embodiments and are not intended to limit the scope of the invention.

Examples of materials, dimensions, assemblies and manufacturing processes are provided for selected parts. All other parts employ that which is known to those skilled in the field of the invention. Those skilled in the art will recognize that many of the examples provided have suitable alternatives which may also be utilized.

Figure 1:
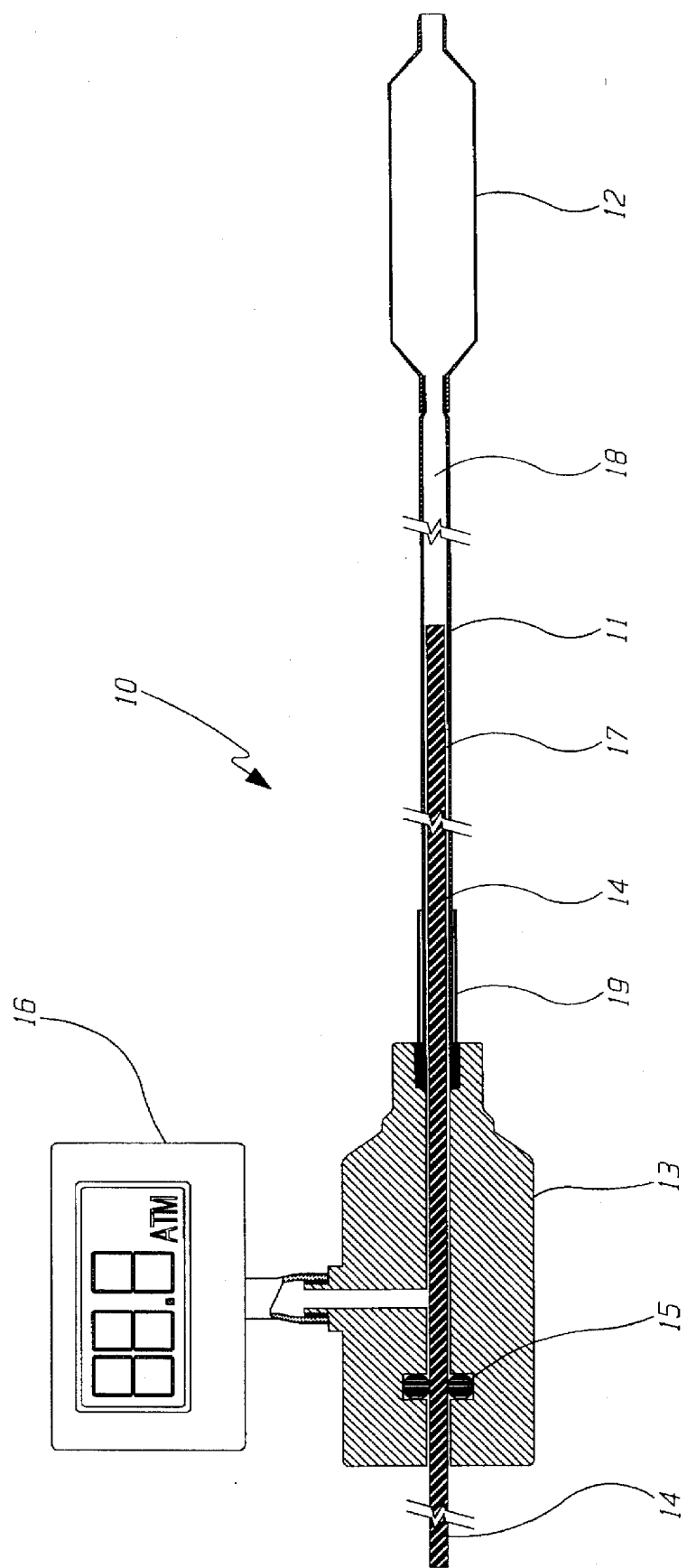
FIG. 1 is a partially-sectioned side view of a generic embodiment of the present invention.

Refer now to FIG. 1 in which a partially-sectioned side view of a generic catheter embodiment 10 is shown. Generic catheter 10 includes an elongate shaft 11 with a balloon 12 connected to its distal end and a manifold 13 connected to its proximal end. A fluid displacement rod 14 is disposed inside the elongate shaft 11 and is longitudinally movable therein. Proximal seal 15 creates a fluid seal between the inside of the elongate shaft 11 and the displacement rod 14 such that longitudinal actuation of displacement rod 14 causes a bolus of liquid 18 to move into or out of the inflatable balloon 12. In particular, when the fluid displacement rod 14 is advanced in the distal direction, the rod 14 displaces liquid bolus 18 into the internal volume of the balloon 12. Further distal advancement of the rod 14 causes the pressure inside the balloon to increase. When the displacement rod 14 is retracted in the proximal direction, liquid bolus 18 exits the balloon and causes the balloon 12 to contract. A static column of fluid 17 links the pressure gauge 16 to the liquid bolus 18 and thus measures the internal pressure of the balloon 12. The term "bolus of liquid" or "liquid bolus" as used in this application is defined as a closed volume of liquid that is relatively large as compared to the static column of fluid 17 between the rod 14 and the inside diameter of the shaft 11.

The generic catheter 10 may take the form of any balloon catheter and may be used in a variety of medical procedures. For example, the generic catheter 10 may take the form of a fixed wire catheter (FIG. 2), an over-the-wire catheter (FIGS. 3a and 3b) or a single-operator-exchange catheter (FIGS. 4a and 4b) and may be used in coronary, peripheral, cerebral and urethral applications. In addition, the generic catheter 10 may incorporate other clinically-significant features such as perfusion or drug delivery capabilities. For the purpose of the following discussion, the exemplary embodiments are directed to a catheter system which is particularly suitable for PTCA procedures. However, with modifications in construction, the generic catheter 10 may be used for other medical applications not fully discussed herein.

The balloon 12 may be constructed in a variety of ways. The material of balloon 10 may be selected from polymers including, but not limited to, polyolefin copolymer, polyester, polyethylene terephthalate, polyethylene, polyether block amide, polyamide, polyimide, nylon, latex and urethane. The balloon 12 may be made by blow-molding a polymer extrusion into the desired shape. A number of ancillary processes may be used to affect the material properties of the balloon 12. For example, the polymer extrusion may be exposed to gamma radiation which alters the polymer infrastructure to provide uniform expansion during blow-molding and additional burst strength when in use. In addition, the molded balloon 12 may be exposed to a low temperature plasma field which alters the surface properties of the balloon 12 to provide enhanced adhesion characteristics. Those skilled in the art will recognize that other materials and manufacturing processes may be used to provide a balloon 12 suitable for use with the present invention.

Similarly, the shaft 11 may be made of several different constructions, materials and dimensions, depending on the performance characteristics desired. The shaft 11 may be made of, for example, an extruded polymer tube, a stainless steel hypotube or a composite material such as stainless steel braid encased in polyimide. To impart different characteristics along the length of the catheter 10, the shaft 11 may incorporate changes in diameter or combine different constructions. For example, the shaft 11 may have a composite proximal section combined with a polymer distal section. Those skilled in the art will recognize that the shaft 11 can take on a wide variety of constructions not fully discussed herein but well known in the art.

Generally, connections between the various polymer components may be made utilizing suitable medical grade adhesives or thermal bonds well known in the art. Connections between metallic components may be made, for example, by utilizing a solder, braze or weld joint.

Manifold 13 may be formed of various polymers such as injection molded polycarbonate. Seal 15 may be made of a conventional sealing material such as silicone rubber and is secured in a recess formed in the manifold 13. The pressure gauge may be secured to the manifold 13 utilizing a threaded connection, an adhesive connection, a thermal weld, or any other suitable means. A strain relief 19 such as a polymer or metallic tube may be secured to the manifold 13 and/or proximal end of the shaft 11 to reduce the tendency of the shaft 11 to kink immediately adjacent the distal end of the manifold 13.

Fluid displacement rod 14 may be in the form of a solid rod, a tube or a combination thereof. For example, fluid displacement rod 14 may be a metallic or polymer rod having a circular cross section. Fluid displacement rod 14 must have a sufficient length to at least partially extend inside the shaft 11 and at least partially extend proximal of the manifold 13. In particular, the fluid displacement rod must have sufficient length to extend proximal of the manifold when the rod 14 is fully displaced in the distal direction. The portion of the rod 14 extending proximal of the manifold 13 provides a handle for the treating physician to grasp and control longitudinal actuation of the rod 14. Preferably, fluid displacement rod 14 extends as far as possible into the shaft 11 to minimize the distance that liquid bolus 18 has to travel and thus increase the responsiveness of the balloon 12. Fluid displacement rod 14 must also have sufficient volume to displace liquid bolus 18 to cause expansion of the balloon 12 when the rod 14 is longitudinally displaced in the distal direction. In addition, fluid displacement rod 14 must have sufficient volume to displace liquid bolus 18 to cause contraction of the balloon 12 when the rod 14 is longitudinally displaced in the proximal direction.

As mentioned previously, pressure gauge 16 is fluidly linked to liquid bolus 18 by way of static fluid column 17. When balloon 12 is under pressure, liquid bolus 18 exerts a force on the static column of fluid 17 which transfers the force to the pressure gauge 16. The cross-sectional area of static fluid column 17 is preferably minimized to reduce the outside profile of the elongate shaft 11. Minimizing the cross-sectional area of static fluid column 17 does not impede the ability of pressure gauge 16 to measure the pressure of liquid bolus 18 and thus the internal pressure of balloon 12 since the static column of fluid 17 merely transfers force from the liquid bolus 18 to the pressure gauge 16 and accordingly, does not flow. Pressure gauge 16 is preferably a low compliance pressure gauge utilizing a piezoelectric crystal transducer.

In practice, generic catheter 10 is used in a manner somewhat similar to conventional balloon catheters. In particular, the steps associated with inserting the device in-vivo and positioning the balloon across the treatment site are essentially the same as with conventional balloon catheters. However, the steps for prepping the catheter 10 and inflating the catheter 10 are different. Note that the prepping methods and the balloon expansion methods of the present invention are independent. That is to say that the prepping method may be used without the expansion method and vice-versa, without compromising the advantages associated with each method.

Prepping a catheter means to replace all the air in the catheter with a liquid such as saline mixed with radiographic contrast media. The generic catheter 10 may, for example, be prepped by filling the catheter with liquid prior to final packaging (discussed below) or the catheter may be prepped by utilizing the prep methods discussed below with reference FIGS. 5 and 6. These prep methods are exemplary only and those skilled in the art will recognize that other prep methods may also be utilized. After the catheter 10 is prepped, the catheter may be inserted in-vivo and positioned across the treatment site in essentially the same manner as a conventional balloon catheter.

With the catheter 10 in position in-vivo, the balloon 12 may be expanded by longitudinally actuating the displacement rod 14. Longitudinal actuation of the displacement rod 14 is accomplished by pushing the rod distally while holding the manifold 13 and the shaft 11 relatively fixed. Since the proximal seal 15 creates a fluid tight seal between the inside of the elongate shaft 11 and the displacement rod 14, longitudinal actuation of displacement rod 14 in the distal direction causes the bolus of liquid 18 to move into the inflatable balloon 12. Further distal advancement of the rod 14 causes the pressure inside the balloon 12 to increase. Accordingly, the balloon 12 is expanded to the desired size and/or pressure as measured by angiography and/or the pressure gauge 16. The static column of fluid 17 links the pressure gauge 16 to the liquid bolus 18 and allows measurement of the internal pressure of the balloon 12. When desired, the treating physician may contract the balloon by reversing the actuation steps. In particular, when the displacement rod 14 is retracted in the proximal direction, liquid bolus 18 exits the balloon and causes the balloon 12 to contract. After the treatment is complete, the catheter 10 is removed in substantially the same manner as conventional balloon catheters.

It is contemplated that the catheter 10 may be prepped prior to final packaging. In other words, the interior of the catheter 10 would be filled with a liquid after final assembly but before final packaging such that the catheter 10 would be pre-prepped upon removal from the packaging. Since many polymers used to manufacture catheters are semi-permeable to liquid and liquid vapor, it is contemplated that the packaging would also be filled with the same or similar liquid in order to prevent liquid egress from the interior of the catheter. Alternatively, the inside of the packaging may be filled with a dissimilar fluid that is not mixable with the fluid inside the catheter. For example, if the catheter is filled with a water base solution, an oil base solution may be placed in the packaging to retard liquid egress from inside the catheter. A further alternative is contemplated in which the packaging may be filled with a liquid saturated gas at a pressure at equilibrium with the interior of the catheter. Under these conditions, there would be no pressure or saturation gradient causing fluid egress from inside the catheter.

Figure 2:
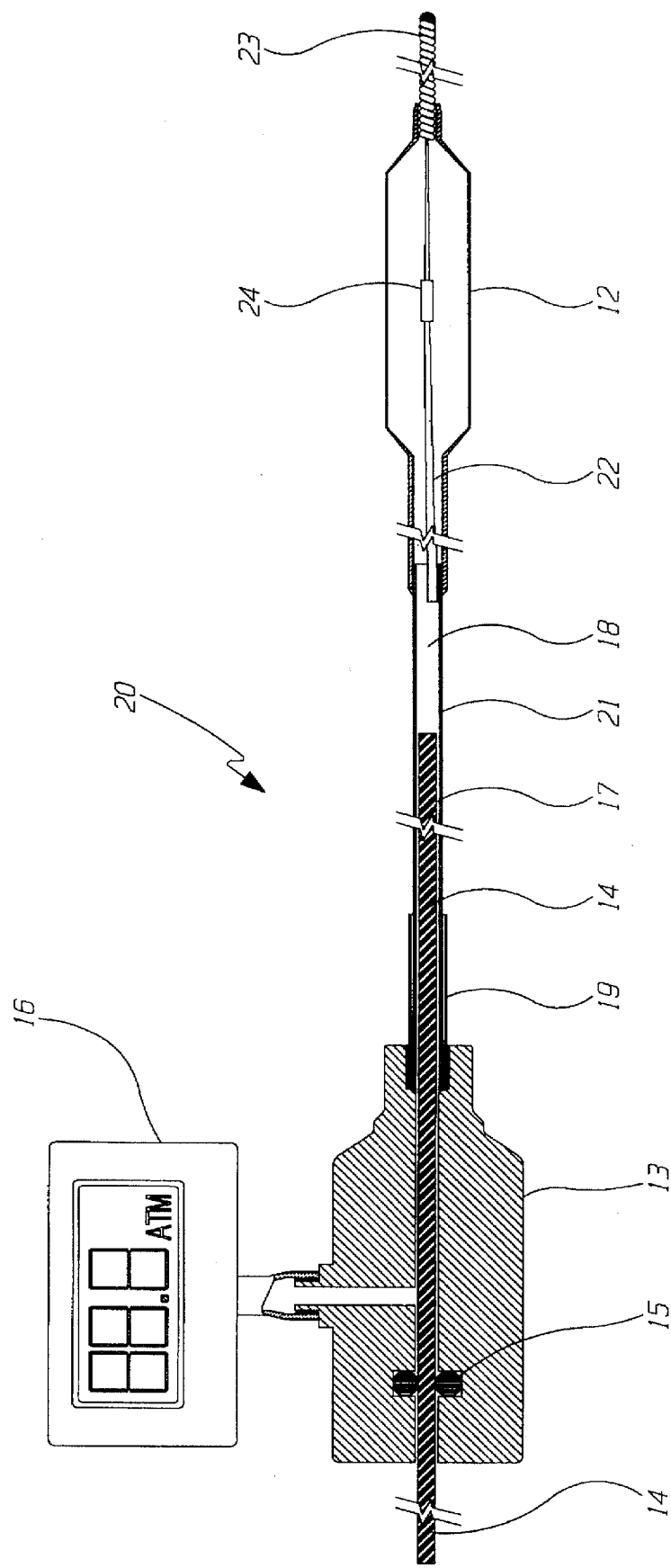

As mentioned previously, generic catheter 10 may take the form of a variety of balloon catheters including a fixed wire type balloon catheter. Refer now to FIG. 2 which shows a partially-sectioned side view of a fixed wire catheter embodiment 20. A more detailed description of a known fixed wire catheter can be found in U.S. Pat. No. 4,943,278 to Euteneuer et al. Fixed wire catheter 20 is similar to generic catheter 10 except for the following differences.

Fixed wire catheter 20 includes an elongate shaft 21 with a balloon 12 sealingly connected to its distal end and a manifold 13 sealingly connected to its proximal end. A strain relief 19 such as a polymer or metallic tube may be secured to the manifold 13 and/or proximal end of the shaft 21 to reduce the tendency of the shaft 21 to kink immediately adjacent the distal end of the manifold 13. A core wire 22 is connected to the distal end of the elongate shaft 21 and extends through the proximal waist of the balloon, traverses the interior of the balloon and terminates with a radiopaque spring tip 23 extending beyond the distal end of the balloon 12. The distal end of the balloon 12 is sealingly connected to the spring tip 23. A radiopaque marker band 24 is secured to the core wire 22 to facilitate radiographic placement of the catheter 20.

Elongate shaft 21 is preferably made of a medical grade metal such as stainless steel or a super elastic alloy such as a Nickel-Titanium alloy having a length of about 44.0 inches, an inside diameter of about 0.014 inches and an outside diameter of about 0.021 inches. Core wire 22 may also be made of a medical grade metal such as stainless steel or a super elastic alloy such as a Nickel-Titanium alloy and may be soldered, brazed or welded to the distal end of the elongate shaft 21. Core wire 22 may have a length of about 14.0 inches and a diameter tapering from about 0.012 inches proximally to about 0.002 inches distally. The spring tip 23 may be coiled about the distal end of the core wire 22 and is preferably made of a radiopaque metal alloy such as an Iridium-Tungsten alloy. Spring tip 23 may be soldered, brazed or welded to the core wire 22 at both ends of the spring coil. Radiopaque marker band 24 is preferably made of Gold, Platinum or Iridium-Tungsten and may be adhesively secured or soldered to core wire 22 at approximately the axial center of the balloon 12.

Figure 3A:
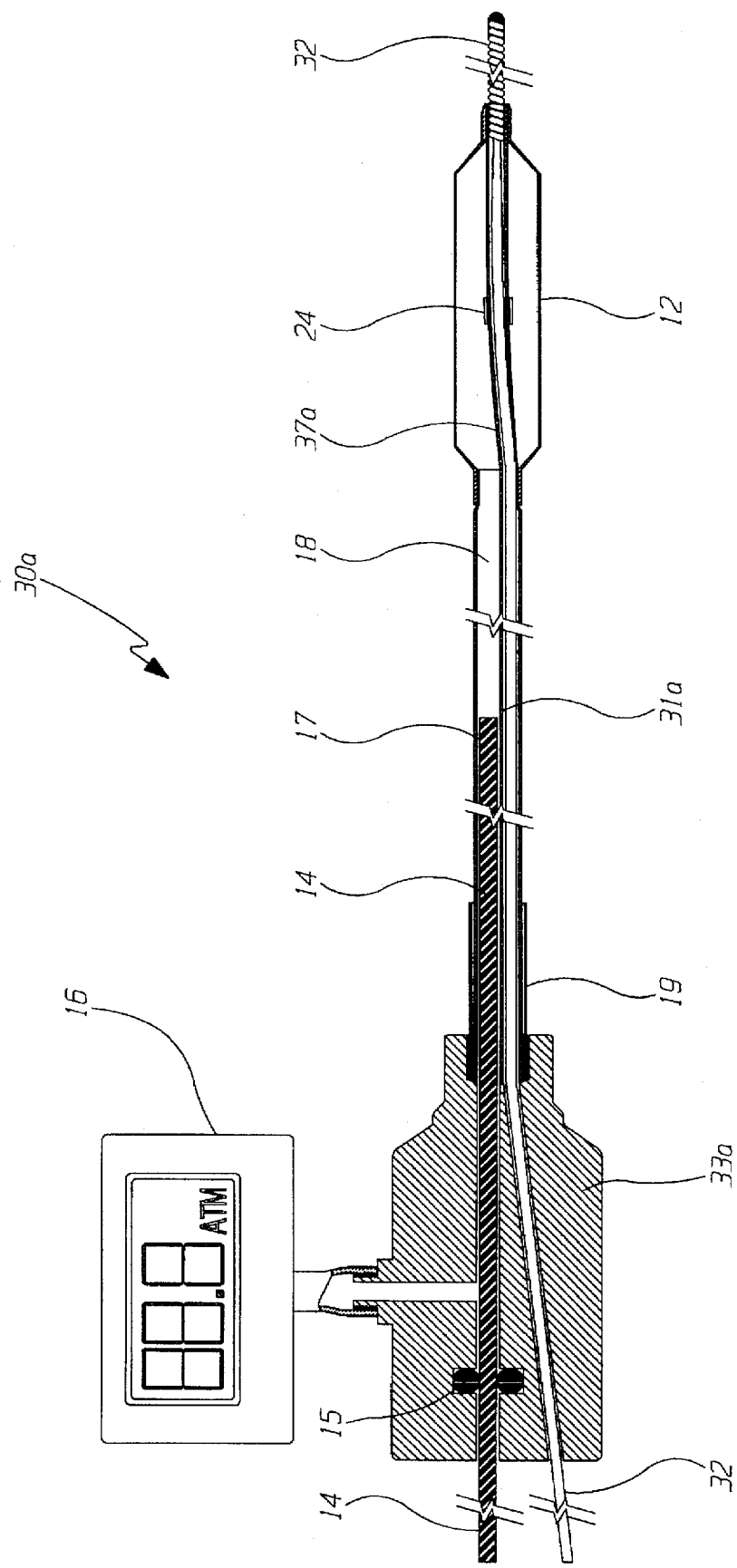

In addition to a fixed wire catheter 20, generic catheter 10 may take the form of an over-the-wire type balloon catheter. Refer now to FIGS. 3a and 3b which show, respectively, partially-sectioned side views of a side-by-side lumen over-the-wire catheter embodiment 30a and a coaxial over-the-wire catheter embodiment 30b. A more detailed description of a known side-by-side lumen over-the-wire catheter can be found in U.S. Pat. No. 5,382,234 to Cornelius et al. and a more detailed description of a known coaxial over-the-wire catheter can be found in U.S. Pat. No. 5,100,381 to Burns. Over-the-wire catheters 30a and 30b are similar to generic catheter 10 except for the following differences.

Side-by-side lumen over-the-wire catheter 30a includes a dual lumen shaft 31a with an inflatable balloon 12 connected to its distal end and a manifold 33a connected to its proximal end. Guide wire 32 passes through manifold 33a, into the dual lumen shaft 31a, through the shaft extension 37a and exits distally of the balloon 12. The distal end of the balloon 12 is sealingly connected to the distal end of the shaft extension 37a and the proximal end of the balloon is sealingly connected to the distal end of the dual lumen shaft 31a. A strain relief 19 such as a polymer or metallic tube may be secured to the manifold 33a and/or the proximal end of the dual lumen shaft 31a to reduce the tendency of the shaft 31a to kink immediately adjacent the distal end of the manifold 33a. A radiopaque marker band 24 may be secured to the shaft extension 37a to facilitate radiographic placement of the catheter 30a.

Dual lumen shaft 31a may be made of a dual lumen extruded polymer or two separate tubes secured together side-by-side. Dual lumen shaft 31a may have a length of about 52.0 inches and an outer diameter of approximately 0.040 inches. Shaft extension 37a may be a partial continuation of the dual lumen shaft 31a or a separate tube secured to the distal end of the dual lumen shaft 31a. Radiopaque marker band 24 is preferably made of Gold, Platinum or Iridium-Tungsten and may be adhesively secured to the shaft extension 37a at approximately the axial center of the balloon 12.

Coaxial over-the-wire catheter 30b includes an elongate shaft 31b with a balloon 12 sealingly connected to its distal end and a manifold 33b sealingly connected to its proximal end. A strain relief 19 such as a polymer or metallic tube may be secured to the manifold 33b and/or the proximal end of the shaft 31b to reduce the tendency of the shaft 31b to kink immediately adjacent the distal end of the manifold 33b. A fluid displacement tube 34b is slidably disposed in elongate shaft 31b. Proximal seal 15 provides a liquid tight seal between the interior of the elongate shaft 31b and the exterior of the displacement tube 34b. A guide wire 32 extends through the interior of the fluid displacement tube 34b, through the distal end of the elongate shaft 31b and exits distally of the balloon 12. Proximal guide wire seal 36b provides a fluid tight seal between the guide wire 32 and the interior of the fluid displacement tube 34b. Distal guide wire seal 37b provides a fluid tight seal between the interior of the balloon 12 and the guide wire 32. With this arrangement of seals 15/36b/37b, longitudinal actuation of displacement tube 34b causes the bolus of liquid 18 to move into or out of the inflatable balloon 12.

Shaft 31b may be formed of a polymer extrusion or composite tube having a length of about 52.0 inches and an outer diameter of about 0.040 inches. Displacement tube 34b may be formed of a reinforced polymer tube having a length of about 50.0 inches, an inner diameter of about 0.018 inches and an outer diameter of about 0.025 inches. Examples of suitable guide wire seals 36b/37b are disclosed in commonly-assigned co-pending patent application Ser. No. 08/443,496 entitled "Single Operator Exchange Perfusion Catheter Having a Distal Catheter Shaft Section" which is fully incorporated herein by reference.

Figure 4B:
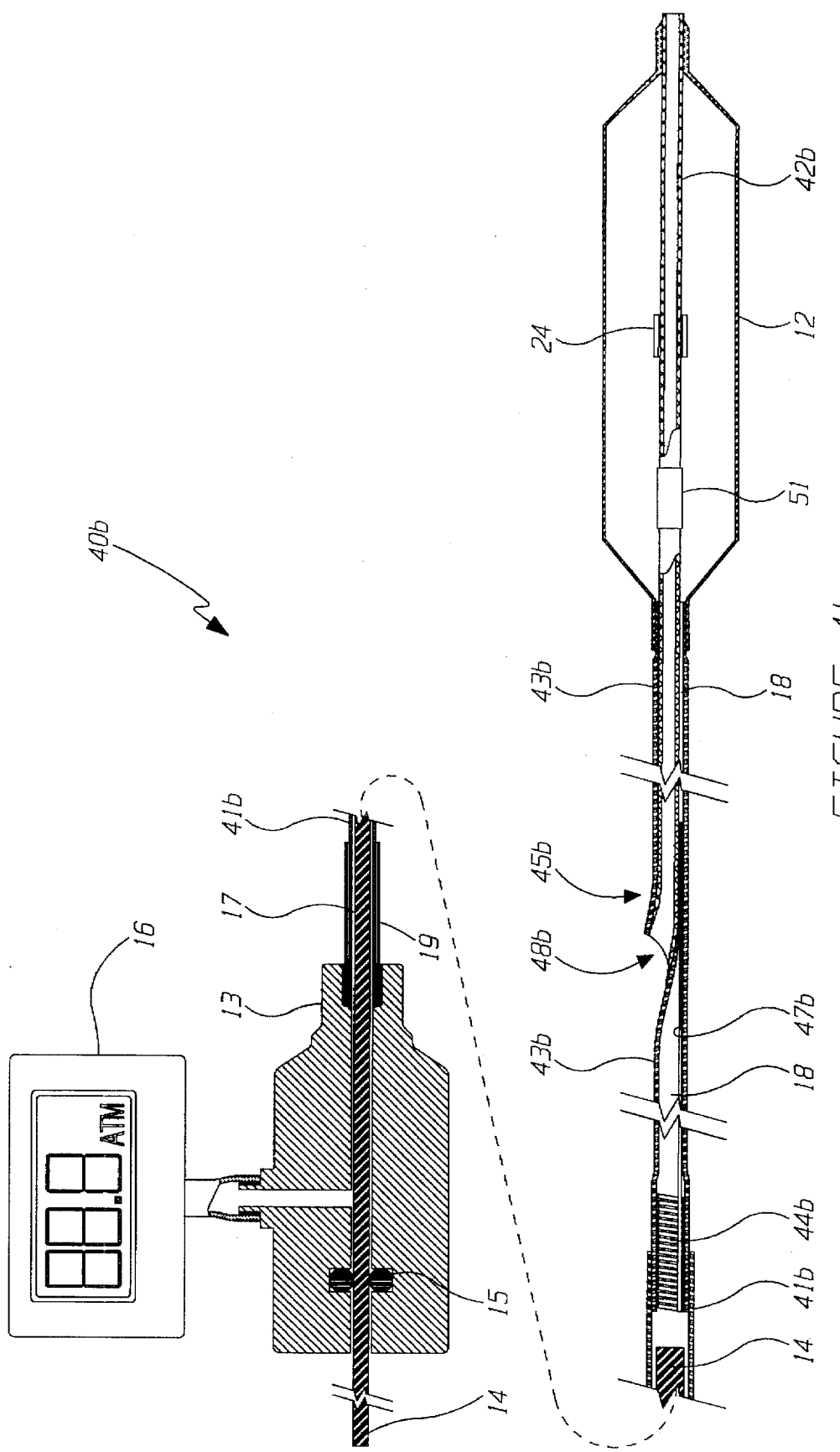

In addition to a fixed wire catheter 20 and an over-the-wire catheters 30a and 30b, generic catheter 10 may take the form of a single-operator-exchange type balloon catheter. Refer now to FIGS. 4a and 4b which show partially-sectioned side views of two single-operator-exchange catheter embodiments. Note that catheter 40a is a generic single-operator-exchange catheter embodiment while catheter 40b is a relatively specific single-operator-exchange catheter embodiment. A more detailed description of a known single-operator-exchange balloon catheter can be found in U.S. Pat. No. 5,156,594 to Keith et al. Single-operator-exchange catheters 40a and 40b are similar to generic catheter 10 except for the following differences.

Single-operator-exchange catheter 40a includes an elongate shaft 41a with a balloon 12 sealingly connected to its distal end and a manifold 13 sealingly connected to its proximal end. A strain relief 19 such as a polymer or metallic tube may be secured to the manifold 13 and/or the proximal end of the shaft 41a to reduce the tendency of the shaft 41a to kink immediately adjacent the distal end of the manifold 13. A guide wire tube 42a has a distal end sealingly connected to the distal end of the balloon and a proximal end defining a proximal guide wire port 48a in communication with the exterior of the catheter 40a and sealingly connected to the elongate shaft 41a. Proximal guide wire port 48a is located at a point substantially distal of the proximal end of the catheter 40a and proximal of the distal end of the catheter 40a. A guide wire (not shown) may traverse the interior of the guide wire tube 42a such that the guide wire enters the proximal guide wire port 48a and exits distally of the balloon 12. A radiopaque marker band 24 may be secured to the guide wire tube 42a to facilitate radiographic placement of the catheter 40a.

Single-operator-exchange catheter 40b includes a proximal shaft section 41b with a manifold 13 connected to its proximal end and a distal shaft section 43b connected to its distal end. A strain relief 19 such as a polymer or metallic tube may be secured to the manifold 13 and/or the proximal end of the shaft 41b to reduce the tendency of the shaft to kink immediately adjacent the distal end of the manifold 13. An additional strain relief 44b may traverse the connection between the proximal shaft 41b and the distal shaft 43b. Strain relief 44b reduces the tendency of the distal shaft 43b to kink immediately adjacent the distal end of the proximal shaft 41b. A core wire 47b has a proximal end rigidly connected to the distal end of the proximal shaft 41b and/or the proximal end of the distal shaft 43b. Core wire 47b transfers longitudinal force from the distal end of the proximal shaft 41b, provides for decreasing diametric stiffness along the length of the distal shaft 43b and acts as a strain relief reducing the propensity of the distal shaft 43b to kink immediately adjacent the crimp section 45b. Guide wire tube 42b is sealingly connected at its distal end to the distal end of the balloon 12. The proximal end of the guide wire tube 42b defines a proximal guide wire port 48b in communication with the exterior of the catheter 40b and sealingly connected to the distal shaft 43b. Proximal guide wire port is located at a point substantially distal of the proximal end of the catheter 40a and preferably about 2.75 inches proximal of the distal end of the catheter 40a. A guide wire (not shown) may traverse the interior of the guide wire tube 42b such that the guide wire enters the proximal guide wire port 48b and exits distally of the balloon 12. A radiopaque marker band 24 may be secured to the guide wire tube 42b to facilitate radiographic placement of the catheter 40b. Optionally, a one-way valve 51 may be connected to the guide wire tube 42b to facilitate prepping the catheter 40b. The incorporation of one-way-valve 51 to facilitate prepping is preferred but not necessary as other suitable prep methods known to those skilled in the art may also be employed. One-way valve 51 and the prepping method are discussed in detail with reference to FIGS. 5a–5c.

Proximal shaft 41b is preferably made of a polyimide-encased stainless steel braid having an inside diameter of approximately 0.0394 inches, an outside diameter of about 0.0466 inches and a length of approximately 44.0 inches. The stainless steel braid embedded in the polyimide preferably has a pick-per-inch ratio ranging from about 50 to about 70. The stainless steel braid is preferably made of woven stainless steel ribbon having a width of approximately 0.005 inches and a height of approximately 0.0007 inches. Manifold 13 may be adhesively secured to the proximal end of the elongate proximal shaft 41b by means of a suitable medical grade adhesive. Manifold 13 is preferably made of injection-molded polycarbonate having an approximately 0.123 inch diameter recess provided for the proximal seal 15 which is preferably made of silicone having an inside diameter of about 0.042 inches and an outside diameter of about 0.142 inches. Pressure gauge 16 preferably incorporates a piezoelectric crystal pressure transducer and a digital readout.

Liquid displacement rod 14 is preferably made of a stainless steel wire surrounded by a Kynar™ tube. The stainless steel wire preferably has a diameter of about 0.019 inches and a length of about 50.0 inches. The tube surrounding the wire preferably has an outside diameter of about 0.038 inches and an inside diameter of about 0.020 inches. When fully actuated in the distal direction, displacement rod 14 preferably may extend to the distal end of the proximal shaft section 41b to minimize the distance liquid bolus 18 has to travel and thus increase the responsiveness of the balloon.

Distal shaft section 43b is preferably made of polyethylene having an outside diameter of about 0.0364 inches tapering to about 0.0335 inches, an inside diameter of about 0.0308 inches tapering to about 0.0277 inches and a length of about 8.0 inches. The proximal end of the distal shaft section 43b may be adhesively secured to the distal end of the proximal shaft segment 41b. Strain relief 44b is preferably made of a stainless steel coil with an outside diameter of about 0.028 inches and a pitch of about 0.068 inches. The stainless steel coil is preferably formed by a coiled ribbon having a width of about 0.019 inches and a height of about 0.003 inches. The core wire 47b is preferably made of stainless steel having a proximal diameter of about 0.012 inches tapering to a distal diameter of about 0.003 inches. The proximal end of the core wire 47b is preferably brazed to the strain relief 44b which in turn is adhesively secured to the inside of the distal shaft segment 43b.

Guide wire tube 42b is preferably made of polyethylene having an outside diameter of about 0.0215 inches, an inside diameter of about 0.0163 inches and a length of about 2.75 inches. The distal end of the guide wire tube 42b is adhesively secured to the distal end of the balloon 12 by a suitable medical grade adhesive. The proximal end of the guide wire tube 42b is preferably thermally bonded to the distal shaft section 43b in a crimped portion 45b of the distal shaft 43b. Balloon 12 is preferably made of a blow-molded polyether-block-amide such as PEBAX™ 7233. The proximal end of the balloon 12 may be adhesively secured to the distal end of the distal shaft segment 43b utilizing a suitable medical grade adhesive. The working portion of the balloon 12 may range in length anywhere from 10 mm to 50 mm and may range in diameter anywhere from 1.0 mm to 10.0 mm.

Refer now to FIGS. 5a–5c which show a partially-sectioned side view of a one-way valve 51 incorporated into the distal section of a balloon catheter such as an over-the-wire or a single-operator-exchange type balloon catheter. One-way-valve 51 may be incorporated into virtually any balloon catheter having a guide wire tube (or similar structure) traversing the interior of the balloon, including some of the balloon catheters discussed previously.

One-way valve 51 may be incorporated into guide wire tube 52 which traverses the interior of the balloon 53a. One-way valve 51 includes an elastic tube 55 disposed about one or more holes 54 in the wall of guide wire tube 52. Elastic tube 55 is preferably made of an elastomer such as Techothane™ 1085A having a length of about 1.2 inches, an inside diameter of about 0.0165 inches and an outside diameter of about 0.023 inches. The elastic tube 55 is preferably centered about two holes 54 formed through one side of the guide wire tube 52 wherein the holes 54 preferably have a diameter of about 0.009 inches. To facilitate prepping, a tubular fitting 56 such as a balloon protector is disposed over folded balloon 53b. A connector 57 such as a luer fitting allows the tubular fitting to be connected to a pressurized fluid source such as a fluid-filled syringe (not shown). Tubular fitting 56 fits snugly about folded balloon 53b such that fluid introduced into the tubular fitting 56 enters into the interior of the guide wire tube 52.

As pressurized fluid enters the guide wire tube 52, elastic tube 55 deflects in an outward direction permitting fluid to flow through holes 54 and into the interior of the catheter and the balloon 53. Elastic tube 55 preferably requires a threshold actuation pressure of greater than one atmosphere of pressure to deflect and permit fluid to flow through holes 54. Having a threshold pressure above one atmosphere allows the balloon 53 to be contracted in a conventional manner (i.e., by pulling a vacuum at the proximal end of the catheter) without drawing any unwanted fluids through the one-way valve 51. Fluid flow from the interior of the balloon 53 to the interior of the guide wire tube 52 is prevented by elastic tube 55 which presses against guide wire tube 52 and forms a seal about holes 54 when the inside pressure of the balloon 53 is greater than the pressure inside the guide wire tube 52. Accordingly, one-way valve 51 permits fluid to flow from the interior of the guide wire tube into the interior of the balloon 53 but does not permit flow from the interior of the balloon 53 to the interior of the guide wire tube 52.

It is contemplated that one-way valve 51 may be located proximal of the balloon if the tubular fitting 56 maintains the balloon 53b in such a contracted state that an insignificant amount of air is trapped inside the balloon 53. In this embodiment, a vacuum source (not shown) such as a vacuum bottle may be connected to the proximal end of the catheter to facilitate filling the catheter shaft and the balloon 53 with liquid. To maximize effectiveness, the vacuum source should be applied prior to introducing pressurized fluid from the syringe.

Refer now to FIG. 6a which shows a partially-sectioned side view of the distal section of a balloon catheter incorporating a one-way valve 61 proximal of the balloon. One-way-valve 61 may be incorporated into virtually any balloon catheter in addition to those discussed above. One-way valve 61 operates based on the same principles as one-way valve 51 discussed with reference to FIGS. 5a–5c. One-way valve 61 is incorporated into a shaft 62 proximal of the balloon 69 and includes one or more holes 64 through the wall of the shaft 62. An elastic tube 65 is disposed within the shaft 62 across the holes 64. When the pressure outside the holes 64 is above one atmosphere relative to the pressure inside the shaft 62, the elastic tube 65 deflects in an inward direction and permits flow through the holes 64 to the interior of the shaft 62. When the pressure inside the shaft 62 is greater than the pressure outside the shaft, the elastic tube 65 presses against the inside of the shaft 62 sealing about holes 64 preventing flow from the interior of the shaft 62 to the exterior of the shaft. Accordingly, one-way valve 61 only permits flow from the exterior of the shaft 62 to the interior of the shaft at pressure gradients above one atmosphere.

Refer now to FIGS. 6c and 6d which show a first embodiment of a system facilitating prepping of a balloon catheter utilizing the one-way valve 61 as shown in FIGS. 6a and 6b. The catheter to be prepped includes an elongate shaft 62 having a manifold 68 connected to its proximal end and a balloon 69 connected to its distal end. The catheter is disposed inside a carrier tube 67 which is conventional for balloon catheter packaging. The distal end of the carrier tube 67 includes a connector 72 to facilitate connection to a pressurized fluid source such as a liquid-filled syringe 63. A passive seal 71 such as an O-ring seal is connected to the inside of the carrier tube 67 at a point proximal of the one-way valve 61. Accordingly, when pressurized fluid is introduced by way of the syringe 63, fluid passes through the valve holes 64 and into the interior of the catheter shaft 62. A vacuum source 66 such as a vacuum bottle may be connected to the manifold 68 to facilitate filling the catheter shaft 62 and the balloon 69 with liquid. To maximize effectiveness, vacuum source 66 applies a vacuum to the interior of the catheter shaft 62 prior to introducing pressurized fluid from the syringe 63.

Refer now to FIGS. 6e and 6f which show a second embodiment of a system facilitating prepping of a balloon catheter utilizing the one-way valve 61 as shown in FIGS. 6a and 6b. As discussed with reference to FIGS. 6c and 6d, catheter shaft 62 includes a manifold 68 connected to its proximal end and a balloon 69 connected to its distal end. A vacuum source 66 may be connected to the manifold 68 to facilitate prepping as discussed previously. A syringe 63 is connected to the carrier tube 67 utilizing connector tubes 84. Connector tubes 84 are in turn connected to active seals 81 and 82 located inside the carrier tube 67. When pressurized fluid is introduced by the syringe 63 through the connector tubes 84, active seals 81 and 82 fluidly seal on either side of the one-way valve 61. In particular, active seals 81 and 82 comprise oppositely-facing balloons which, upon inflation, seal about the catheter shaft 62 and the interior of the carrier tube 67. A small hole 83 is placed in one of the active seals 81 or 82 such that fluid under pressure from syringe 63 seeps into the chamber defined between active seals 81 and 82. The fluid which seeps from hole 83 is under sufficient pressure to deflect the elastic tube 65 and cause fluid to flow into the holes 64 and into the interior of the shaft 62, thus displacing air inside the catheter shaft 62 with liquid from the pressurized fluid source 63.

Refer now to FIGS. 7a and 7b which show plan views of two mechanisms which facilitate manipulation of the fluid displacement rod 14. In FIG. 7a, displacement mechanism 71a includes an engagement member 72a which engages the fluid displacement rod 14 when moved in the distal direction and accordingly causes fluid displacement rod 14 to also move in the distal direction. When moved in the proximal direction, engagement member 72a disengages the fluid displacement rod 14 and slides thereon. Manifold 13 (which is connected to the proximal end of the shaft 11) may include a thumb ring 73a and engagement member 72a may includes grooves 74a for receiving fingers such that the engagement member 72a may be grasped with middle and first fingers and the manifold may be grasped with the thumb. Accordingly, simple contraction of the hand causes the engagement member 72a to move distally relative to the manifold 13 and thus cause fluid displacement rod to move distally effecting expansion of the balloon. A metal tube 75a may be secured over the proximal portion of the rod 14 to add integrity to the displacement mechanism and avoid damage to the rod 14.

Refer now to FIG. 7b which shows displacement mechanism 71b which facilitates advancement of fluid displacement rod 14. Displacement mechanism 71b includes an engagement member 72b which incorporates a push button lock mechanism 73b. Push button lock mechanism 73b is normally locked onto the fluid displacement rod 14 such that depression of the push button on the lock mechanism 73b causes disengagement of the fluid displacement rod 14. A proximal portion 74b of the fluid displacement rod 14 is threaded and is engaged by threads (not shown) inside manifold 13. Accordingly, the fluid displacement rod 14 is manually displaced in the distal direction with the push button on the lock mechanism 73b fully depressed (i.e., disengaged). Once an initial pressure is reached inside the balloon, the push button on the lock mechanism 73b is released, thus engaging fluid displacement rod 14 and the assembly 72b/14 is rotated, causing advancement of the fluid displacement rod by virtue of threaded portion 74b engaging the threads inside manifold 13. Accordingly rotation of the assembly 14/72b advances the rod 14 to cause the pressure inside the balloon to increase.

While the specification describes the preferred constructions, materials, dimensions, methods of manufacture and methods of practice, those skilled in the art will appreciate the scope and spirit of the invention with reference to the appended claims.

What is claimed is:

1. A balloon catheter, comprising:
   a. an elongate tubular member having a proximal end and a distal end;
   b. a balloon connected to the distal end of the elongate tubular member, the balloon having an interior in fluid communication with the inside of the elongate tubular member;
   c. a fluid displacement rod having a portion thereof slidably disposed in the tubular member such that the balloon may be expanded upon longitudinal actuation of the rod; and
   d. a seal connected to the proximal end of the tubular member and disposed about the displacement rod to create a liquid seal between the inside of the tubular member and the displacement rod.

2. A balloon catheter as in claim 1, further comprising:
   e. a pressure gauge connected to the proximal end of the elongate tubular member and in fluid communication with the interior of the balloon.

3. A balloon catheter as in claim 2, wherein the seal is an o-ring type seal.

4. A balloon catheter as in claim 2, wherein the seal is a gap tolerance type seal.

5. A balloon catheter as in claim 2, wherein the elongate tubular member contains a guide wire lumen extending at least partially therethrough.

6. A balloon catheter as in claim 5, wherein the guide wire lumen extends the full length of the elongate tubular member.

7. A balloon catheter as in claim 5, wherein the guide wire lumen extends from a point distal of the proximal end of the elongate tubular member to the distal end of the elongate tubular member.

8. A balloon catheter as in claim 5, further comprising:
   f. a one-way-valve connected to the distal end of the elongate tubular member, the one-way-valve permitting a pressurized fluid to flow from the guide wire lumen to the interior of the balloon while preventing the pressurized fluid to flow from the interior of the balloon to the guide wire lumen.

9. A balloon catheter as in claim 8, wherein the proximal end of the guide wire lumen is releasable connected to a fluid plug and the distal end of the guide wire lumen is releasable connected to a pressurized fluid source.

10. A balloon catheter as in claim 9, wherein the pressurized liquid source is releasable connected to the distal end of the guide wire lumen with a tubular member disposed about the balloon.

11. A balloon catheter as in claim 10, wherein the tubular member retains the balloon in a contracted state.

12. A balloon catheter as in claim 11, wherein a portion of the elongate tubular member traverses the interior of the balloon.

13. A balloon catheter as in claim 12, wherein the one-way-valve is connected to the portion of the elongate tubular member which traverses the interior of the balloon.

14. A balloon catheter as in claim 13, wherein the one-way-valve includes an elastomer tube disposed about a hole in the portion of the elongate tubular member which traverses the interior of the balloon.

15. A balloon catheter as in claim 2, wherein the elongate tubular member contains a core wire fixed therein, the core wire having a distally mounted spring tip.

16. A method of using a balloon catheter, comprising the steps of:
   a. providing a balloon catheter wherein the balloon catheter includes:
      i. an elongate tubular member having a proximal end and a distal end;
      ii. a balloon connected to the distal end of the elongate tubular member, the balloon having an interior in fluid communication with the inside of the elongate tubular member;
      iii. a fluid displacement rod having a portion thereof slidably disposed in the tubular member such that the balloon may be expanded upon longitudinal actuation of the rod; and
      iv. a seal connected to the proximal end of the tubular member and disposed about the displacement rod to create a liquid seal between the inside of the tubular member and the displacement rod;
   b. inserting the balloon catheter into a vascular system of a patient;
   c. positioning the balloon catheter adjacent a treatment site in the vascular system;
   d. displacing the rod to at least partially expand the balloon;
   e. displacing the rod to at least partially contract the balloon; and
   f. withdrawing the balloon catheter from the vascular system.

17. A balloon catheter, comprising:
   a. an elongate shaft having a proximal end, a distal end and a lumen disposed therein, the lumen extending from a point distal of the proximal end of the elongate shaft to the distal end of the elongate shaft;
   b. a balloon connected to the distal end of the elongate shaft, the balloon having an interior; and
   c. a one-way-valve connected to the distal end of the shaft, the one-way-valve permitting a pressurized fluid to flow from the lumen to the interior of the balloon while preventing the pressurized fluid to flow from the interior of the balloon to the lumen.

18. A balloon catheter as in claim 17, wherein one end of the lumen is releasable connected to a fluid plug and the other end of the lumen is releasable connected to a pressurized liquid source.

19. A balloon catheter as in claim 18, wherein a portion of the shaft traverses the interior of the balloon.

20. A balloon catheter as in claim 19, wherein the one-way-valve is connected to the portion of the shaft which traverses the interior of the balloon.

21. A balloon catheter as in claim 20, wherein the one-way-valve includes an elastomer tube disposed about a hole in the portion of the shaft which traverses the interior of the balloon.

22. A balloon catheter as in claim 17, wherein the proximal end of the lumen is releasable connected to a fluid plug and the distal end of the lumen is releasable connected to a pressurized fluid source.

23. A balloon catheter as in claim 22, wherein the pressurized liquid source is releasable connected to the distal end of the lumen with a tubular member disposed about the balloon.

24. A balloon catheter as in claim 23, wherein the tubular member retains the balloon in a contracted state.

25. A balloon catheter as in claim 24, wherein a portion of the shaft traverses the interior of the balloon.

26. A balloon catheter as in claim 25, wherein the one-way-valve is connected to the portion of the shaft which traverses the interior of the balloon.

27. A balloon catheter as in claim 26, wherein the one-way-valve includes an elastomer tube disposed about a hole in the portion of the shaft which traverses the interior of the balloon.

28. A method of prepping a balloon catheter, comprising the steps of:
   a. providing a balloon catheter having a proximal end and a distal end, the balloon catheter including:
      i. an elongate shaft having a proximal end, a distal end and a lumen disposed therein;
      ii. a balloon connected to the distal end of the elongate shaft, the balloon having an interior; and
      iii. a one-way-valve connected to the distal end of the shaft, the one-way-valve permitting a pressurized fluid to flow from the lumen to the interior of the balloon while preventing the pressurized fluid to flow from the interior of the balloon to the lumen;
   b. providing a pressurized fluid source containing fluid therein;
   c. connecting the pressurized fluid source to the distal end of the lumen in the elongate shaft of the balloon catheter;
   d. plugging the proximal end of the lumen in the elongate shaft of the balloon catheter; and
   e. forcing fluid from the pressurized fluid source into the lumen such that the fluid passes into the lumen, through the one-way-valve and into the interior of the balloon.

29. A balloon catheter, comprising: a sealed chamber; a balloon connected to the distal end of the chamber and in fluid communication with the chamber;
   and a fluid displacement member disposed at least partially within the sealed chamber to displace fluid into or out of the balloon.

* * * * *